US011980648B2

(12) United States Patent
Wright et al.

(10) Patent No.: US 11,980,648 B2
(45) Date of Patent: May 14, 2024

(54) COMPOSITIONS INCLUDING GINSENOSIDE 20(S)-RG3 AND METHODS OF USING GINSENOSIDE 20(S)-RG3 TO INHIBIT ALPHA HERPESVIRUS

(71) Applicant: MIDDLE TENNESSEE STATE UNIVERSITY, Murfreesboro, TN (US)

(72) Inventors: Stephen Wright, Murfreesboro, TN (US); Shannon Smith, Murfreesboro, TN (US); Karen Maynard, Murfreesboro, TN (US); Elliot Altman, Rockvale, TN (US)

(73) Assignee: MIDDLE TENNESSEE STATE UNIVERSITY, Murfreesboro, TN (US)

( * ) Notice: Subject to any disclaimer, the term of this patent is extended or adjusted under 35 U.S.C. 154(b) by 95 days.

(21) Appl. No.: 17/338,882

(22) Filed: Jun. 4, 2021

(65) Prior Publication Data
US 2021/0379132 A1 Dec. 9, 2021

Related U.S. Application Data

(60) Provisional application No. 63/036,380, filed on Jun. 8, 2020.

(51) Int. Cl.
| | |
|---|---|
| *A61K 36/258* | (2006.01) |
| *A61K 31/52* | (2006.01) |
| *A61K 31/522* | (2006.01) |
| *A61K 31/662* | (2006.01) |
| *A61K 31/675* | (2006.01) |
| *A61K 31/704* | (2006.01) |
| *A61K 31/7125* | (2006.01) |
| *A61P 31/22* | (2006.01) |

(52) U.S. Cl.
CPC ............ *A61K 36/258* (2013.01); *A61K 31/52* (2013.01); *A61K 31/522* (2013.01); *A61K 31/662* (2013.01); *A61K 31/675* (2013.01); *A61K 31/704* (2013.01); *A61K 31/7125* (2013.01); *A61P 31/22* (2018.01)

(58) Field of Classification Search
None
See application file for complete search history.

(56) References Cited

FOREIGN PATENT DOCUMENTS

CN 108815218 A * 11/2018 ............ A61K 31/704
WO WO-2008010668 A1 * 1/2008 ............. A61K 31/56

OTHER PUBLICATIONS

Yang, Hui, et al. "Ginsenoside-Rb2 and 20 (S)-Ginsenoside-Rg3 from Korean red ginseng prevent rotavirus infection in newborn mice." J. Microbiol. Biotechnol. (2018): 391-396. (Year: 2018).*

Tian, Jingwei, et al. "20 (S)-ginsenoside Rg3, a neuroprotective agent, inhibits mitochondrial permeability transition pores in rat brain." Phytotherapy Research: An International Journal Devoted to Pharmacological and Toxicological Evaluation of Natural Product Derivatives 23.4 (2009): 486-491. (Year: 2009).*

Au, Eugene, and Sacks, Stephen L. "Therapeutic options for herpes simplex infections." Current Infectious Disease Reports; Dordrecht vol. 5, Iss. 1, (2003): 22-27. DOI:10.1007/s11908-003-0061-3 (Year: 2003).*

Cernik, Christina, Kelly Gallina, and Robert T. Brodell. "The treatment of herpes simplex infections: an evidence-based review." Archives of internal medicine 168.11 (2008): 1137-1144. (Year: 2008).*

Xin-Mei C, Chang-Zheng Z, Xiao-Ping Z (2012) New Progress on the Pharmacological and Pharmacokinetical Study of Ginsenoside Rg3. J Drug Metabol Toxicol 3:114. doi:10.4172/2157-7609. 1000114 (Year: 2012).*

Akhtar et al., Viral entry mechanisms: cellular and viral mediators of herpes simplex virus entry. *FEBS J* 276, 7228-7236 (2009).

Bak et al., Neuroprotective effects of 20(S)-protopanaxadiol against glutamate-induced mitochondrial dysfunction in PC12 cells. *Int J Mol Med* 37, 378-386 (2016).

Bender et al., Herpes simplex virus glycoprotein B binds to cell surfaces independently of heparan sulfate and blocks virus entry. *J Virol* 79, 11588-11597 (2005).

Bookstaver et al., Management of Viral Central Nervous System Infections: A Primer for Clinicians. *J Cent Nerv Syst Dis* 9, 1179573517703342 (2017).

Chattopadhyay et al., Recent advancements for the evaluation of anti-viral activities of natural products. *N Biotechnol* 25, 347-368 (2009).

Chen et al., Saponins from stems and leaves of Panax ginseng prevent obesity via regulating thermogenesis, lipogenesis and lipolysis in high-fat diet-induced obese C57BL/6 mice. *Food Chem Toxicol* 106, 393-403 (2017).

Chen et al., Ginsenoside Rh2 Targets EGFR by Up-Regulation of miR-491 to Enhance Anti-tumor Activity in Hepatitis B Virus-Related Hepatocellular Carcinoma. *Cell Biochem Biophys* 72, 325-331 (2015).

Cho et al., Protective effects of red ginseng extract against vaginal herpes simplex virus infection. *J Ginseng Res* 37, 210-218 (2013).

Coleman et al., The effects of Panax ginseng on quality of life. *J Clin Pharm Ther* 28, 5-15 (2003).

Dragos et al., Phytomedicine in Joint Disorders. *Nutrients* 9, 70 (2017).

Faral-Tello et al., Cytotoxic, virucidal, and antiviral activity of South American plant and algae extracts. *ScientificWorldJournal* 2012, 174837 (2012).

(Continued)

*Primary Examiner* — Bethany P Barham
*Assistant Examiner* — Peter Anthopolos
(74) *Attorney, Agent, or Firm* — MUETING RAASCH GROUP

(57) ABSTRACT

This disclosure describes a composition including the ginsenoside 20(S)-Rg3 (also referred to herein as Rg3) and methods of using such a composition. In some embodiments, the composition may be used to treat or prevent an alpha herpesvirus including, for example, herpes simplex virus (HSV)-1 and HSV-2. In some embodiments, the composition is substantially free of other ginsenosides.

20 Claims, 2 Drawing Sheets

(56) References Cited

OTHER PUBLICATIONS

Fu, Biotransformation of ginsenoside Rb1 to Gyp-XVII and minor ginsenoside Rg3 by endophytic bacterium *Flavobacterium* sp. GE 32 isolated from Panax ginseng. *Lett Appl Microbiol* 68, 134-141 (2019).

Ha et al., Determination of 22 ginsenosides in ginseng products using ultra-high-performance liquid chromatography. *J Chromatogr Sci* 51, 355-360 (2013).

Han et al., The Ginsenoside Derivative 20(S)-Protopanaxadiol Inhibits Solar Ultraviolet Light-Induced Matrix Metalloproteinase-1 Expression. *J Cell Biochem* 118, 3756-3764 (2017).

Hien et al., Ginsenoside Rg3 inhibits tumor necrosis factor-alpha-induced expression of cell adhesion molecules in human endothelial cells. *Pharmazie* 65, 699-701 (2010).

Hogestyn et al., Contributions of neurotropic human herpesviruses herpes simplex virus 1 and human herpesvirus 6 to neurodegenerative disease pathology. *Neural Regen Res* 13, 211-221 (2018).

Im et al., Ginseng, the natural effectual antiviral: Protective effects of Korean Red Ginseng against viral infection. *J Ginseng Res* 40, 309-314 (2016).

Joo et al., Novel roles of ginsenoside Rg3 in apoptosis through downregulation of epidermal growth factor receptor. *Chem Biol Interact* 233, 25-34 (2015).

Kang S, Song MJ, Min H. Antiviral activity of ginsenoside Rg3 isomers against gammaherpesvirus through inhibition of p38- and JNK-associated pathways. *J Functional Foods* 2018;40:219-28.

Kang et al., Stimulation of TRAF6/TAK1 degradation and inhibition of JNK/AP-1 signalling by ginsenoside Rg3 attenuates hepatitis B virus replication. *Int J Biochem Cell Biol* 45, 2612-2621 (2013).

Kim et al., Ginsenoside Rg3 restores hepatitis C virus-induced aberrant mitochondrial dynamics and inhibits virus propagation. *Hepatology* 66, 758-771 (2017).

Koelle, Vaccines for herpes simplex virus infections. *Curr Opin Investig Drugs* 7, 136-141 (2006). Abstract only.

Kuo et al., Samarangenin B from Limonium sinense suppresses herpes simplex virus type 1 replication in Vero cells by regulation of viral macromolecular synthesis. *Antimicrob Agents Chemother* 46, 2854-2864 (2002).

Kwon et al., Selective toxicity of ginsenoside Rg3 on multidrug resistant cells by membrane fluidity modulation. *Arch Pharm Res* 31, 171-177 (2008).

Liang et al., Inhibitory effects of Ginsenoside Rb1 on apoptosis caused by HSV-1 in human glioma cells. *Virol Sin* 27, 19-25 (2012).

O'Donnell et al., The Importance of Heparan Sulfate in Herpesvirus Infection. *Virol Sin* 23, 383-393 (2008).

Peng et al., Stereoisomers of Saponins in Panax notoginseng (Sanqi): A Review. *Front Pharmacol* 9, 188 (2018).

Piret et al., Resistance of herpes simplex viruses to nucleoside analogues: mechanisms, prevalence, and management. *Antimicrob Agents Chemother* 55, 459-472 (2011).

Quan et al., Isolation and characterization of novel ginsenoside-hydrolyzing glycosidase from *Microbacterium esteraromaticum* that transforms ginsenoside Rb2 to rare ginsenoside 20(S)-Rg3. *Antonie Van Leeuwenhoek* 104, 129-137 (2013).

Reay et al., A systematic review of research investigating the physiological and psychological effects of combining Ginkgo biloba and Panax ginseng into a single treatment in humans: Implications for research design and analysis. *Brain Behav* 9, e01217 (2019).

Sedy et al., Cross-regulation between herpesviruses and the TNF superfamily members. *Nat Rev Immunol* 8, 861-873 (2008).

Shin et al., Chemical diversity of ginseng saponins from Panax ginseng. *J Ginseng Res* 39, 287-298 (2015).

Song et al., Antiviral activity of ginsenosides against coxsackievirus B3, enterovirus 71, and human rhinovirus 3. *J Ginseng Res* 38, 173-179 (2014).

Song et al., Enhancement of immune responses to influenza vaccine (H3N2) by ginsenoside Re. *Int Immunopharmacol* 10, 351-356 (2010).

Soon-Tae at al. "Panax ginseng enhances cognitive performance in Alzheimer Disease" *Alzheimer Disease and Associated Disorders*, 2008, 3:222-26.

Sun et al., Red notoginseng: higher ginsenoside content and stronger anticancer potential than Asian and American ginseng. *Food Chem* 125, 1299-1305 (2011).

Uchida et al., A double mutation in glycoprotein gB compensates for ineffective gD-dependent initiation of herpes simplex virus type 1 infection. *J Virol* 84, 12200-12209 (2010).

Wang et al., "The Processing of Panax Notoginseng and the Transformation of its Saponin Components", *Food Chem.* 2012;132:1808-1813.

Wei et al., Stereospecificity of ginsenoside Rg3 in promotion of the immune response to ovalbumin in mice. *Int Immunol* 24, 465-471 (2012).

Wright et al., Inhibition of Herpes Simplex Viruses, Types 1 and 2, by Ginsenoside 20(S)-Rg3, *J. Microbiol. Biotechnol.*, 30(1), 101-108, 2020.

Yang et al., Ginsenoside-Rb2 and 20(S)-Ginsenoside-Rg3 from Korean Red Ginseng Prevent Rotavirus Infection in Newborn Mice. *J Microbiol Biotechnol* 28, 391-396 (2018).

\* cited by examiner

FIG. 2

Incubation of HSV-1 with Bioactive Compound

COMPOSITIONS INCLUDING GINSENOSIDE 20(S)-RG3 AND METHODS OF USING GINSENOSIDE 20(S)-RG3 TO INHIBIT ALPHA HERPESVIRUS

CROSS-REFERENCE TO RELATED APPLICATIONS

This application claims the benefit of U.S. Provisional Application Ser. No. 63/036,380, filed Jun. 8, 2020, which is incorporated by reference herein in its entirety

BACKGROUND

Infections by herpes simplex viruses have an immense impact on humans, ranging from self-limiting, benign illness to serious, life-threatening diseases. For example, Herpes Simplex Virus (HSV), an alpha herpesvirus, causes both cold sores and genital infections. HSV-1 is the usual causative agent of cold sores, while HSV-2 is the usual causative agent of genital infections. According to the most recent statistics from the Centers for Disease Control and Prevention (CDC) National Center for Health Statistics (NCHS) during 2015-2016 in the US, the prevalence of herpes simplex virus type 1 (HSV-1) was 47.8% of the population, and prevalence of herpes simplex virus type 2 (HSV-2) was 11.9% of the population. According to the most recent statistics by the World Health Organization (WHO) there are about 3.7 billion people under the age 50 (67%) infected with HSV-1 worldwide and an estimated 417 million people aged 15-49 (11%) infected with HSV-2 worldwide. While there are over 10 drugs that are used to treat HSV infections, the primary agent is Acyclovir. All of the current treatment regimens for HSV involve very problematic expensive drugs that can cause adverse side effects. Thus safer cheaper drugs are desperately needed.

While nucleoside analog drugs (including, for example, acyclovir and penciclovir and their respective prodrugs valacyclovir and famciclovir) are available as HSV treatments, resistance to these drugs is increasing and the current drug regimens cause adverse side effects. Moreover, currently no vaccine exists.

SUMMARY OF THE INVENTION

This disclosure describes a composition including the ginsenoside 20(S)-Rg3 (also referred to herein as Rg3) and methods of using such a composition. In some embodiments, the method preferably includes using the composition as an anti-alpha herpesvirus agent or for treating or preventing an alpha herpesvirus infection.

In one aspect, this disclosure describes a composition including 20(S)-Rg3 and a pharmaceutically acceptable carrier.

In another aspect, this disclosure describes a composition including purified 20(S)-Rg3. In some embodiments, the composition may further include a pharmaceutically acceptable carrier.

In some embodiments, the composition includes at least 95% (weight/weight) 20(S)-Rg3, at least 97% (w/w) 20(S)-Rg3, at least 98% (w/w) 20(S)-Rg3, at least 99% (w/w) 20(S)-Rg3, at least 99.5% (w/w) 20(S)-Rg3, or at least 99.9% (w/w) 20(S)-Rg3 with respect to the total weight of ginsenosides in the composition.

In some embodiments, the composition includes a second active agent. An exemplary second active agent is an anti-herpes agent. In some embodiments, an anti-herpes viral agent includes acyclovir, penciclovir, valacyclovir, famciclovir, ganciclovir, valganciclovir, foscarnet, cidofovir, and/or fomivirsen.

In some embodiments, when the composition includes a pharmaceutically acceptable carrier or a second active agent or both, the pharmaceutically acceptable carrier or the second active agent or both are a non-naturally occurring compound.

In some embodiments, the composition includes an extract prepared from a plant in the genus *Panax*.

In another aspect, this disclosure describes a method for treating or preventing an alpha herpesvirus infection in a subject. In some embodiments, the method includes administering to the subject the composition as described herein. In some embodiments, method includes administering to the subject a composition including 20(S)-Rg3. In some embodiments, the alpha herpesvirus infection comprises herpes simplex virus-1 (HSV-1), herpes simplex virus-2 (HSV-2), or both.

In some embodiments, the method includes administering a composition including 20(S)-Rg3 before a second active agent is administered. In some embodiments, the method includes administering a composition including 20(S)-Rg3 at the same time a second active agent is administered. In some embodiments, the method includes administering a composition including 20(S)-Rg3 after a second active agent is administered. In some embodiments, 20(S)-Rg3 and a second active agent may be administered in the same composition.

In a further aspect, this disclosure describes use of 20(S)-Rg3 for preparation of a medicament for the treatment or prevention of an alpha herpesvirus infection.

In yet another aspect, this disclosure describes use of 20(S)-Rg3 for preparation of a medicament for the treatment or prevention of an infection with herpes simplex virus-1 (HSV-1) or herpes simplex virus-2 (HSV-2) or both.

The term "substantially free" (as in the phrase "substantially free of another ginsenoside") means that there is less than 20% (by weight) of the another ginsenoside (including, for example, an isomer of 20(S)-Rg3) present, more preferably, there is less than 10% (by weight) of the another ginsenoside present, more preferably, there is less than 5% (by weight) of another ginsenoside present, and most preferably, there is less than 1% (by weight) of another ginsenoside present.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

BRIEF DESCRIPTION OF THE FIGURES

FIG. 2 shows exemplary percent inhibition of HSV-1 following incubation with a bioactive compound. HSV-1 and the bioactive compound (valacyclovir or 20(S)-Rg3) were applied directly to cells simultaneously (no incubation) or the virus and compound were incubated together for 1 hour or 4 hours prior to being added to the cells.

DETAILED DESCRIPTION OF ILLUSTRATIVE EMBODIMENTS

Figure 1:
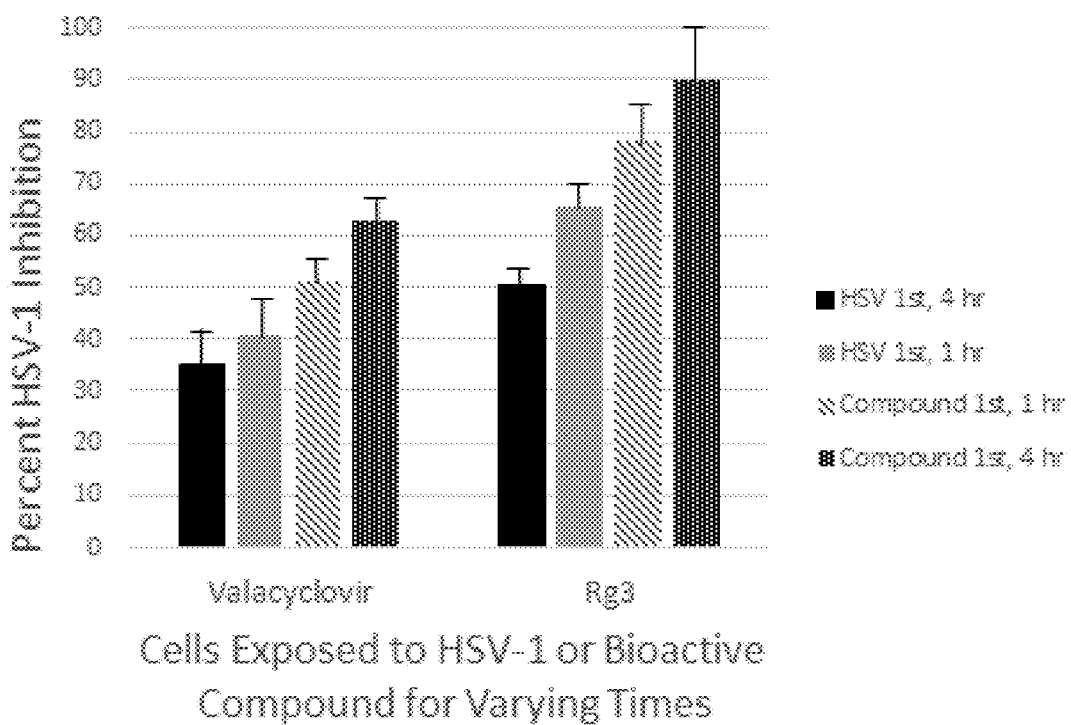
FIG. 1 shows exemplary results of HSV-1 inhibition by valacyclovir or 20(S)-Rg3. Cells were exposed to HSV-1 for 1 hour or 4 hours prior to addition of a bioactive compound (valacyclovir or 20(S)-Rg3); results are shown in the black bars and grey bars, respectively. Alternatively, cells were exposed to the bioactive compounds (valacyclovir or 20(S)-Rg3) for 1 hour or 4 hours, before HSV-1 was added; results are shown in the hatched bars and stippled bars, respectively.

This disclosure describes a composition including the ginsenoside 20(S)-Rg3 (also referred to herein as Rg3) and methods of using such a composition. In some embodiments, the method preferably includes using the composition as an anti-alpha herpesvirus agent or for treating or preventing an alpha herpesvirus infection. In some embodiments, an alpha herpesvirus includes, for example, herpes simplex virus (HSV)-1 and HSV-2.

Ginsenosides

Ginsenosides derived from *Panax ginseng* Meyer have previously been documented to inhibit several viruses and bolster immune defenses. However, no ginsenoside has been identified with activity against herpes simplex virus (HSV) at a non-toxic concentration.

For example, the ginsenoside metabolite 20(S)-protopanaxadiol has been reported to have pharmacological activity (Han et al. J Cell Biochem 2017; 118:3756-64). Protopanaxadiol has also been found to be an effective anti-oxidant that preserves healthy mitochondrial function (Bak et al. Int J Mol Med 2016; 37:378-86) as well as providing protection for UV-associated skin wrinkling (Han et al. J Cell Biochem 2017; 118:3756-64). As further described in Example 1, the toxicity and anti-herpes activity of protopanaxadiol were investigated. While 25 μM 20(S)-protopanaxadiol was found to be non-toxic, consistent with the report of Bak et al. (Int J Mol Med 2016; 37:378-86), protopanaxadiol failed to have any protective effect against HSV-1.

The ginsenoside Rb1 has been reported to decrease the apoptotic effects of HSV-1 in a human glioma cell line (Liang et al. Virol Sin 2012; 27:19-25). However, as reported in Example 1, Rb1 caused greater than 10% Vero cell death when used at a concentration higher than 50 μM and that minimal inhibition (23%) of HSV-1 occurred at this non-toxic concentration.

Chen et al. (Cell Biochem Biophys 2015; 72:325-31) reported that Rh2 suppressed tumor growth in hepatitis B virus hepatocellular carcinoma cells. The protopanaxatriols Re, Rf, and Rg2 had inhibitory effects on coxsackie B 3 virus and human rhinovirus 3 at 100 μg/mL (Song et al. J Ginseng Res 2014; 38:173-9). Ginsenoside-Re has been reported to have anti-influenza virus activity due to enhancing immune responses after infection in mice (Song et al. Int Immunopharmacol 2010; 10:351-6). None of these ginsenosides exhibited at least 50% inhibition of HSV-1, however, as reported in Example 1.

In contrast, Example 1 describes dramatic inhibition of HSV-1 and HSV-2 by 20(S)-Rg3 at concentrations non-toxic to cells.

20(S)-Rg3

20(S)-Rg3 is a ginsenoside, one of a group of glycosylated triterpenes, also known as saponins, found in the roots of a plant in the genus *Panax*. 20(S)-Rg3 and 20(R)-Rg3 have the formula $C_{42}H_{72}O_{13}$ and are hydrolytic products of ginsenoside-Rb2. The structures of 20(S)-Rg3 (also sometimes referred to as 20(S)-ginsenoside-Rg3) and 20(S)-Rg3, 20(R)-Rg3 (also sometimes referred to as 20(R)-ginsenoside-Rg3) are shown below:

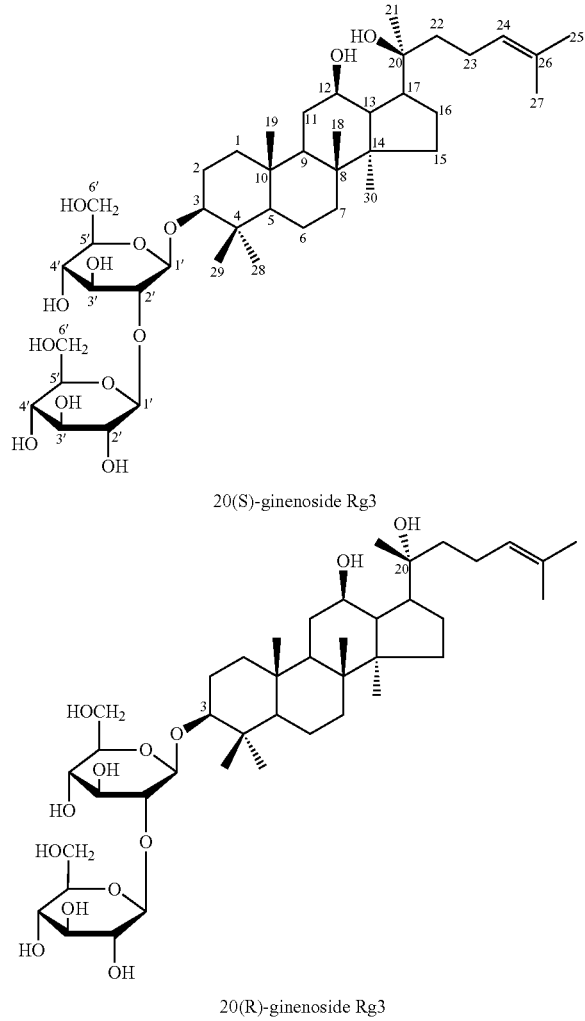

20(S)-ginenoside Rg3

20(R)-ginenoside Rg3

20(S)-Rg3 and 20(R)-Rg3 (collectively, "Rg3" are epimers of each other depending on the position of the hydroxyl (OH) group on carbon-20, and stereospecificity of Rg3 has been observed with respect to its pharmacological actions. (Wei et al. International immunology, 2012; 24(7):465-471.)

One of the bioactive properties attributed to 20(S)-Rg3 is anti-cancer effects by decreasing drug efflux from a cancer cell line (Kwon et al. Arch Pharm Res 2008; 31:171-7). In that study, 20(S)-Rg3 was found to be cytotoxic for human carcinoma cells KB V20C when used at 120 μM, but this concentration had no effect on normal WI 38 cells. 20(R)-Rg3/20(S)-Rg3 has been determined to have potent anti-inflammatory activity by down-regulation of cytokine expression (Hien et al. Pharmazie 2010; 65:699-701). 20(S)-Rg3 has also been recognized to inhibit several virus life cycles. 20(S)-Rg3, but not 20(R)-Rg3, was reported to prevent rotavirus infection in mice, presumably due to mediation of immune responses (Yang et al. J Microbiol Biotechnol 2018; 28:391-6). Studies have shown that 20(R)-Rg3/20(S)-Rg3 reduces the expression of epidermal growth factor receptor on cells (Joo et al. Chem Biol Interact 2015; 233:25-34). Such down-regulation of host receptors may impact viral attachment to a potential host. Kim et al. (Hepatology 2017; 66:758-71) described 20(R)-Rg3/20(S)-Rg3 as a potential therapeutic agent for hepatitis C virus. 20(R)-Rg3/20(S)-Rg3 restored normal mitochondrial processes that hepatitis C had disrupted, thus helping prevent chronic virus infection. 20(R)-Rg3/20(S)-Rg3 also has been reported to inhibit hepatitis B virus capsid maturation by interfering with pro-inflammatory cytokine expression (Kang et al. Int J Biochem Cell Biol 2013; 45:2612-21). Kang et al. (J Functional Foods 2018; 40:219-28) determined that 20(R)-Rg3 and 20(S)-Rg3 prevented the replication of a murine gammaherpesvirus, likely through inhibition of cellular signaling pathways.

A crude extract of Korean Red ginseng prepared in water and delivered by oral gavage has been documented to inhibit HSV-1 vaginal infection in mice (Cho et al. J Ginseng Res 2013; 37:210-8). The mechanism for the protective effects of the ginseng extract was suggested to involve stimulation of immune responses, particularly interferon γ and natural killer cells. However, the compound responsible for this inhibition was unknown.

Example 1 shows purified 20(S)-Rg3 effectively curtails replication by both HSV-1 and HSV-2 and that 20(S)-Rg3 prevents mortality in mice caused by infection with HSV. Moreover, at concentrations of 250 μM and less—almost 10 times the dose effective to curtail replication—exposure to 20(S)-Rg3 was non-toxic and even had a proliferative effect on cells.

In some embodiments, as further described below, this disclosure is directed to compositions including purified and partially purified forms of 20(S)-Rg3. In some embodiments, this disclosure is directed to the use of those compositions and to crude plant extracts including 20(S)-Rg3 for use in treating or preventing alpha herpesvirus infection including, for example, HSV infection.

Isolation or Synthesis of 20(S)-Rg3

In some embodiments, 20(S)-Rg3 can be isolated from ginseng (that is, from a root of a plant in the genus *Panax*). In some embodiments, the ginseng may preferably be an older plant; older ginseng plants have been observed to produce more of the precursor compounds that can be converted to Rg3 by steaming. In some embodiments, ginsenoside Rb1 may be isolated from ginseng and converted to 20(S)-Rg3 by steaming. For example, ginsenoside Rb1 may be converted to ginsenoside Rd and ginsenoside Rd may be converted to 20(R)-Rg3/20(S)-Rg3. (See Wang et al. Food Chem. 2012; 132:1808-1813.) Natural ginseng contains both Rb1 and Rd, but there is a lot more Rb1 than Rd. In some embodiments, ginsenoside Rd may be isolated from ginseng and converted to 20(R)-Rg3/20(S)-Rg3 by steaming. (See id.) In some embodiments, 20(R)-Rg3/20(S)-Rg3 may be further purified from other ginsengs and/or 20(S)-Rg3 may be further purified from a 20(R)-Rg3/20(S)-Rg3 mixture including, for example, by using either traditional chromatography or high performance liquid chromatography (HPLC).

In some embodiments, 20(S)-Rg3 can be obtained from the hydrolysis of another ginsenoside. It also is expected that 20(S)-Rg3 can be enzymatically synthesized using the appropriate plant enzymes. In some embodiments, ginsenoside Rb2 may be a starting material. See for example Quan et al. Antonie Van Leeuwenhoek, 2013; 104:129-37. In some embodiments, ginsenoside Rb1 may be a starting material. See for example Fu, Letters in Applied Microbiology, 2019, 68:134-41. In some embodiments, steam may be used to convert ginsenoside Rb1 to ginsenoside Rd to 20(R)-Rg3/20(S)-Rg3.

Composition Including 20(S)-Rg3

In one aspect, this disclosure describes a composition including 20(S)-Rg3. In some embodiments, the composition may be a pharmaceutical composition that includes 20(S)-Rg3 as an active agent. The pharmaceutical composition may further include a pharmaceutically acceptable carrier.

A pharmaceutically acceptable carrier can include, for example, an excipient, a diluent, a solvent, an accessory ingredient, a stabilizer, a protein carrier, or a biological compound. Nonlimiting examples of a protein carrier includes keyhole limpet hemocyanin (KLH), bovine serum albumin (BSA), ovalbumin, or the like. Nonlimiting examples of a biological compound which can serve as a carrier include a glycosaminoglycan, a proteoglycan, and albumin. The carrier can be a synthetic compound, such as dimethyl sulfoxide or a synthetic polymer, such as a polyalkyleneglycol. Ovalbumin, human serum albumin, other proteins, polyethylene glycol, or the like can be employed as the carrier. In some embodiments, the pharmaceutically acceptable carrier includes at least one compound that is not naturally occurring or a product of nature.

In some embodiments, the active agent 20(S)-Rg3 may be formulated in combination with one or more additional active agents. In some embodiments, the composition includes as a first active agent 20(S)-Rg3, and a second active agent that can include one or more of, for example, other anti-viral agent(s). Other anti-viral agents may include, for example, another anti-herpes viral agent. An anti-herpes viral agent may include, for example acyclovir, penciclovir, valacyclovir, famciclovir, ganciclovir, valganciclovir, foscarnet, cidofovir, or fomivirsen, or a combination thereof. More generally, any known therapeutic or prophylactic agent can be included as additional active agent. The action of the additional active agent in the combination therapy can be cumulative to the 20(S)-Rg3 or it can be complementary, for example to manage side effects or other aspects of a patient's medical condition.

A composition of the invention may preferably include at least one compound that is not naturally occurring or a product of nature. In some embodiments, the composition includes at least one non-naturally occurring therapeutic or prophylactic agent.

In some embodiments, the composition includes 20(S)-Rg3. In some embodiments, the composition includes a partially purified plant extract that contains 20(S)-Rg3. In some embodiments, the composition includes purified 20(S)-Rg3.

In some embodiments, a composition including purified 20(S)-Rg3 may include other ginsenosides (including, for example 20(R)-Rg3) but such a composition includes at least 50% (weight/weight) 20(S)-Rg3, at least 60% (w/w) 20(S)-Rg3, at least 70% (w/w) 20(S)-Rg3, at least 80% (w/w) 20(S)-Rg3, at least 90% (w/w) 20(S)-Rg3, at least 95% (w/w) 20(S)-Rg3, at least 97% (w/w) 20(S)-Rg3, at least 98% (w/w) 20(S)-Rg3, at least 99% (w/w) 20(S)-Rg3, at least 99.5% (w/w) 20(S)-Rg3, or at least 99.9% (w/w) 20(S)-Rg3 with respect to the total weight of ginsenosides in the composition. In one exemplary embodiment, the composition includes 50% (w/w) 20(R)-Rg3 and 50% (w/w) 20(S)-Rg3.

In some embodiments, a composition including purified 20(S)-Rg3 may also include 20(R)-Rg3. When the composition including purified 20(S)-Rg3 includes 20(R)-Rg3 and 20(S)-Rg3 (20(R)-Rg3/20(S)-Rg3), the composition includes at least 90% (w/w) 20(R)-Rg3/20(S)-Rg3, at least 95% (w/w) 20(R)-Rg3/20(S)-Rg3, at least 97% (w/w) 20(R)-Rg3/20(S)-Rg3, at least 98% (w/w) 20(R)-Rg3/20(S)-Rg3, at least 99% (w/w) 20(R)-Rg3/20(S)-Rg3, at least 99.5% (w/w) 20(R)-Rg3/20(S)-Rg3, or at least 99.9% (w/w) 20(R)-Rg3/20(S)-Rg3 with respect to the total weight of ginsenosides in the composition.

In some embodiments, the purity of the ginsenoside can be evaluated using high performance liquid chromatography (HPLC).

The active agent may be formulated in a pharmaceutical composition and then, in accordance with the method of the invention, administered to a subject in a formulation adapted to a chosen route of administration. Such a formulation includes, but is not limited to, a formulation suitable for oral, rectal, vaginal, topical, nasal, ophthalmic or parental (including subcutaneous, intramuscular, intraperitoneal, and intravenous) administration.

A formulation may be conveniently presented in unit dosage form and may be prepared by any of the methods well-known in the art of pharmacy. All methods include the step of bringing the active agent into association with a pharmaceutical carrier. In some embodiments, a formulation may be prepared by uniformly and intimately bringing the active compound into association with a liquid carrier, a finely divided solid carrier, or both, and then, if necessary, shaping the product into the desired formulation.

A formulation of the present invention suitable for oral administration can be presented as discrete units such as tablets, troches, capsules, lozenges, wafers, or cachets, each containing a predetermined amount of the active agent as a powder or granules, as liposomes, or as a solution or suspension in an aqueous liquor or non-aqueous liquid such as a syrup, an elixir, an emulsion, or a draught. The tablets, troches, pills, capsules, and the like can also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it can further contain a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, sugar, and the like. A syrup or elixir can contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent can be incorporated into sustained-release preparations and devices.

A formulation suitable for parenteral administration conveniently include a sterile aqueous preparation of the active agent, or dispersions of sterile powders of the active agent, which are preferably isotonic with the blood of the recipient. Parenteral administration of 20(S)-Rg3 (e.g., through an I.V. drip) is one form of administration. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

A nasal spray formulation includes purified aqueous solutions of the active agent with preservative agents and isotonic agents. Such formulation may be adjusted to a pH and isotonic state compatible with the nasal mucous membranes. A formulation for rectal or vaginal administration may be presented as a suppository with a suitable carrier such as cocoa butter, or hydrogenated fats or hydrogenated fatty carboxylic acids. An ophthalmic formulation may be prepared by a similar method for a nasal spray formulation, except that the pH and isotonic factors are preferably adjusted to match that of the eye. A topical formulation may include the active agent dissolved or suspended in one or more media such as mineral oil, petroleum, polyhydroxy alcohols, or other bases used for topical pharmaceutical formulations.

Methods of Using a Composition Including 20(S)-Rg3

In another aspect, this disclosure provides methods of using a composition including 20(S)-Rg3. In some embodiments, the method includes using the composition as an anti-alpha herpesvirus agent. In some embodiments, a method of using the composition includes administering the composition to a subject. In some embodiments, a method of using the composition includes treating or preventing an alpha herpesvirus infection including, for example, HSV infection, in a subject.

Administration

20(S)-Rg3 can be administered to a subject alone or in a pharmaceutical composition that includes 20(S)-Rg3 and a pharmaceutically acceptable carrier. 20(S)-Rg3 can be introduced into the subject either systemically or at the site of alpha herpesvirus infection including, for example, HSV infection. The active agent (20(S)-Rg3 alone or in combination with one or more additional active agents) may be administered to a human or animal subject, including a domestic or domesticated mammal or other animal, in an amount effective to produce the desired effect. 20(S)-Rg3 or a composition including 20(S)-Rg3 can be administered in a variety of routes, including orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Local administration can include topical administration, administration by injection, or perfusion or bathing of an organ or tissue, for example.

A composition including, for example, a formulation, can be administered as a single dose or in multiple doses. Useful dosages of the active agents can be determined by comparing their in vitro activity and the in vivo activity in animal models. Methods for extrapolation of effective dosages in mice, and other animals, to humans are known in the art.

In some embodiments, a composition including 20(S)-Rg3 that includes other ginsenosides (including, for example 20(R)-Rg3) may preferably include at least 95% 20(S)-Rg3, at least 97% 20(S)-Rg3, at least 98% 20(S)-Rg3, or at least 99% 20(S)-Rg3. In some embodiments, the purity of the ginsenoside can be evaluated using high performance liquid chromatography (HPLC).

In some embodiments, a composition that includes 20(S)-Rg3 that is administered to a subject can include other ginsenosides (including, for example 20(R)-Rg3). In some embodiments, such a composition may preferably include at least 95% 20(S)-Rg3, at least 97% 20(S)-Rg3, at least 98% 20(S)-Rg3, or at least 99% 20(S)-Rg3. In some embodiments, a composition that is administered to a subject may be substantially free of or completely free of other ginsenosides (including, for example 20(R)-Rg3). Additionally or alternatively, 20(S)-Rg3 that is administered to a subject can be substantially free or completely free of other ginsenosides (including, for example 20(R)-Rg3).

Dosage levels of the active agent, including but not limited to 20(S)-Rg3, in the pharmaceutical compositions of this invention can be varied so as to obtain an amount of the active agent which is effective to achieve the desired therapeutic response for a particular subject, composition, and mode of administration, without being toxic to the subject. The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the 20(S)-Rg3, the age, sex, weight, condition, general health and prior medical history of the subject being treated, and like factors well known in the medical arts.

Dosages and dosing regimens that are suitable for other ginsenosides may also suitable for therapeutic or prophylactic administration of 20(S)-Rg3.

In some embodiments, 20(S)-Rg3 may be administered in a dosage of at least 0.01 mg 20(S)-Rg3/kg body weight, at least 0.05 mg/kg, at least 0.1 mg/kg, or at least 1 mg/kg, or at least 5 mg/kg; and up to 1 mg/kg, up to 5 mg/kg, or up to 10 mg/kg.

In some embodiments, 20(S)-Rg3 may be administered in a form sufficient to provide a concentration of 20(S)-Rg3 in the blood of at least 1 $\mu$M, at least 5 $\mu$M, at least 10 $\mu$M, at least 15 $\mu$M, or at least 20 $\mu$M; and up to 5 $\mu$M, up to 10 $\mu$M, up to 15 $\mu$M, up to 20 $\mu$M, up to 25 $\mu$M, up to 50 $\mu$M, or more.

In an exemplary embodiment, 20(S)-Rg3 may be administered in a form sufficient to provide a concentration of 20(S)-Rg3 in a range of 15 $\mu$M to 20 $\mu$M in the composition. In an exemplary embodiment, a 1 mg/kg dose corresponds to a concentration of 17.8 $\mu$M in a typical 70 kg human adult with a blood volume of 5 L.

20(S)-Rg3 can also be administered as an extract obtained from a plant source, such as a ginseng root. Dosages and dosing regimens that are suitable for ginseng roots are likewise suitable for therapeutic prophylactic administration of plant extracts containing 20(S)-Rg3. For example, in some embodiments, 4.5 grams of extract per day may be administered. In some embodiments, examples which can form the basis for determining dosages and dosing regiments for 20(S)-Rg3 may be found in Reay et al, "A systematic review of research investigating the physiological and psychological effects of combining *Ginkgo biloba* and *Panax ginseng* into a single treatment in humans: Implications for research design and analysis" *Brain and Behavior,* 2019, 9:e01217, or Soon-Tae at al. "*Panax ginseng* enhances cognitive performance in Alzheimer Disease" *Alzheimer Disease and Associated Disorders,* 2008, 3:222-26.

Anti-HSV Activity and Related Methods

At the time of the invention, ginsenosides were known to have anti-viral effects, but the efficacy of ginsenosides generally and 20(S)-Rg3 against HSV was unknown prior to the present work. Example 1 demonstrates that purified 20(S)-Rg3 effectively curtails replication by both HSV-1 and HSV-2 and that 20(S)-Rg3 prevents mortality in mice caused by infection with HSV.

This disclosure therefore provides a method for treating or an alpha herpesvirus infection including, for example, HSV infection, in a subject by administering to a subject a composition comprising 20(S)-Rg3 in an amount effective to treat or prevent an alpha herpesvirus infection, inhibit an alpha herpesvirus infection, or alleviate the symptoms of an alpha herpesvirus infection. Administration of the composition may be performed before, during, or after a subject develops an alpha herpesvirus infection.

In some embodiments, the method is a therapeutic method for treating a subject suffering from an alpha herpesvirus infection by administering 20(S)-Rg3 to the subject in an amount effective to treat the alpha herpesvirus infection. In another embodiment, the therapeutic method includes administering 20(S)-Rg3 to a subject who has an alpha herpesvirus infection in an amount effective to inhibit, slow, or reverse replication of an alpha herpesvirus. Therapeutic treatment is initiated after the development of an alpha herpesvirus infection. Treatment initiated after the development of an alpha herpesvirus infection may result in decreasing the severity of the symptoms or completely removing the symptoms. In some embodiments, treatment initiated after the development of an alpha herpesvirus infection may result in preventing death of the subject.

In some embodiments, 20(S)-Rg3 may be administered prophylactically, for example, as a HSV-preventive agent, in an amount effective to prevent or delay the development of an alpha herpesvirus infection in a subject. Treatment that is prophylactic, for instance, can be initiated before a subject develops an alpha herpesvirus infection or manifests symptoms or an alpha herpesvirus infection. An example of a subject that is at particular risk of developing an alpha herpesvirus infection is a person who has been exposed to an alpha herpesvirus via mucous membrane-contact or non-intact-skin contact with the virus, contact with material including the virus, or contact with a person infected with the virus.

Administration of 20(S)-Rg3 to treat or an alpha herpesvirus infection can occur before, during, and/or after other treatments. Such combination therapy can involve the administration of 20(S)-Rg3 before, during and/or after the use of another active agent including, for example, another anti-viral agent. Other anti-viral agents may include, for example, another anti-herpes viral agent. An anti-herpes viral agent may include, for example acyclovir, penciclovir, valacyclovir, famciclovir, ganciclovir, valganciclovir, foscarnet, cidofovir, or fomivirsen, or a combination thereof. The administration of 20(S)-Rg3 can be separated in time from the administration of an additional anti-viral agent or another therapeutic agent by hours, days, or even weeks; alternatively, the two or more agents can be administered concurrently, either together in the same composition or in separate compositions.

Compositions and Methods for Veterinary Use

Any of the compositions or methods described herein that include 20(S)-Rg3 can be used in veterinary applications. Veterinary uses in domestic or domesticated animals (including small animals such as cats, dogs, and other pets, as well as large animals such as cows, horses, pigs, and other livestock), as well as wild animals (for example, animals housed in zoos) to treat or prevent an alpha herpesvirus infection are examples of contemplated applications. Exemplary compositions for veterinary use may contain, in addition to 20(S)-Rg3, other anti-viral compounds, as well as other medications.

Kits

In a further aspect, this disclosure describes includes a kit that contains 20(S)-Rg3 and instructions for use. In some embodiments, the instructions for use provide instructions for use in the treatment or prevention of an alpha herpesvirus infection including, for example, an HSV-1 or HSV-2 infection. Optionally, the kit includes a pharmaceutically acceptable carrier. The carrier may be separately provided, or it may be present in a composition that includes 20(S)-Rg3. Optionally, the kit may further include one or more additional active agents which can be co-administered with the 20(S)-Rg3. The one or more active agents may have cumulative or complementary activities, as described in more detail elsewhere herein.

The invention is defined in the claims. However, below there is provided a non-exhaustive listing of non-limiting exemplary aspects. Any one or more of the features of these aspects may be combined with any one or more features of another example, embodiment, or aspect described herein.

Exemplary Aspects

Aspect 1 is a composition comprising purified 20(S)-Rg3.

Aspect 2 is the composition of Aspect 1, the composition further comprising a pharmaceutically acceptable carrier.

Aspect 3 is a composition comprising 20(S)-Rg3 and a pharmaceutically acceptable carrier.

Aspect 4 is the composition of any one of the preceding Aspects, wherein the composition includes at least 50% (weight/weight) 20(S)-Rg3, at least 60% (w/w) 20(S)-Rg3, at least 70% (w/w) 20(S)-Rg3, at least 80% (w/w) 20(S)-Rg3, at least 90% (w/w) 20(S)-Rg3, at least 95% (w/w) 20(S)-Rg3, at least 97% (w/w) 20(S)-Rg3, at least 98% (w/w) 20(S)-Rg3, or at least 99% (w/w) 20(S)-Rg3, with respect to the total weight of ginsenosides in the composition.

Aspect 5 is the composition of any one of the preceding Aspects, wherein the composition comprises a second active agent.

Aspect 6 is the composition of Aspect 5, wherein the second active agent comprises an anti-herpes viral agent.

Aspect 7 is the composition of Aspect 5 or 6, wherein the second active agent comprises at least one anti-herpes viral agent selected from the group consisting of acyclovir, penciclovir, valacyclovir, famciclovir, ganciclovir, valganciclovir, foscarnet, cidofovir, and fomivirsen.

Aspect 8 is the composition of any one of the preceding Aspects wherein the composition comprises a pharmaceutically acceptable carrier or a second active agent or both, and wherein the pharmaceutically acceptable carrier or the second active agent or both are a non-naturally occurring compound.

Aspect 9 is the composition of any one of the preceding Aspects wherein the composition comprises an extract prepared from a plant in the genus *Panax.*

Aspect 10. A method for treating or preventing an alpha herpesvirus infection in a subject, the method comprising: administering to the subject the composition of any one of Aspects 1 to 9; wherein the alpha herpesvirus infection comprises herpes simplex virus-1 (HSV-1), herpes simplex virus-2 (HSV-2), or both.

Aspect 11. A method for treating or preventing an alpha herpesvirus infection in a subject, the method comprising: administering to the subject a composition comprising 20(S)-Rg3; wherein the alpha herpesvirus infection comprises herpes simplex virus-1 (HSV-1), herpes simplex virus-2 (HSV-2), or both.

Aspect 12 is the method of Aspect 11, wherein the composition comprises an extract prepared from a plant in the genus *Panax*.

Aspect 13 is the method of Aspect 11 or Aspect 12, wherein the composition further comprises a pharmaceutically acceptable carrier.

Aspect 14 is the method of any one of Aspects 11 to 13, wherein the composition comprises purified 20(S)-Rg3.

Aspect 15 is the method of Aspect 14, wherein the composition includes at least 50% (weight/weight) 20(S)-Rg3, at least 60% (w/w) 20(S)-Rg3, at least 70% (w/w) 20(S)-Rg3, at least 80% (w/w) 20(S)-Rg3, at least 90% (w/w) 20(S)-Rg3, at least 95% (w/w) 20(S)-Rg3, at least 97% (w/w) 20(S)-Rg3, at least 98% (w/w) 20(S)-Rg3, at least 99% (w/w) 20(S)-Rg3, at least 99.5% (w/w) 20(S)-Rg3, or at least 99.9% (w/w) 20(S)-Rg3 with respect to the total weight of ginsenosides in the composition.

Aspect 16 is the method of any one of Aspects 10 to 15, wherein the method further comprises administering to the subject a second active agent.

Aspect 17 is the method of Aspect 16, wherein the second active agent comprises an anti-herpes viral agent.

Aspect 18 is the method of Aspect 16 or 17, wherein the second active agent comprises at least one anti-herpes viral agent selected from the group consisting of acyclovir, penciclovir, valacyclovir, famciclovir, ganciclovir, valganciclovir, foscarnet, cidofovir, and fomivirsen.

Aspect 19 is the method of any one of Aspects 16 to 18, wherein the composition comprising 20(S)-Rg3 is administered before the second active agent is administered, wherein the composition comprising 20(S)-Rg3 is administered at the same time the second active agent is administered, and/or wherein the composition comprising 20(S)-Rg3 is administered after the second active agent is administered.

Aspect 20 is the method of any one of Aspects 16 to 19, wherein the 20(S)-Rg3 and the second active agent are administered in the same composition.

Aspect 21 is the method of any one of Aspects 11 to 20, wherein the composition comprises a pharmaceutically acceptable carrier or a second active agent or both, and wherein the pharmaceutically acceptable carrier or the second active agent or both are a non-naturally occurring compound.

Aspect 22 is the use of 20(S)-Rg3 for preparation of a medicament for the treatment or prevention of an alpha herpesvirus infection.

Aspect 23 is the use of 20(S)-Rg3 for preparation of a medicament for the treatment or prevention of an infection with herpes simplex virus-1 (HSV-1) or herpes simplex virus-2 (HSV-2) or both.

The present invention is illustrated by the following examples. It is to be understood that the particular examples, materials, amounts, and procedures are to be interpreted broadly in accordance with the scope and spirit of the invention as set forth herein.

EXAMPLES

Example 1

This Example describes the evaluation of 12 purified ginsenosides from *Panax ginseng* for inhibition of herpes simplex viruses types 1 and 2 (HSV-1 and HSV-2), and the identification of the strong inhibitory effect of Ginsenoside 20(S)-Rg3 on both herpes simplex viruses.

The most prevalent ginsenosides found in natural (white) and steamed (red) ginseng include Rb1, Rb2, Rb3, Rc, Rd, Re, Rf, Rg1, 20(R)-Rg2, 20(S)-Rg2, 20(R)-Rg3, 20(S)-Rg3, 20(R)-Rh1, 20(S)-Rh1, 20(R)-Rh2 and 20(S)-Rh2. The 20(R)-Rg2, 20(S)-Rg2, 20(R)-Rg3, 20(S)-Rg3, 20(R)-Rh1, 20(S)-Rh1, 20(R)-Rh2 and 20(S)-Rh2 ginsenosides are conversion products that are generated when white ginseng is converted by steaming into red ginseng.

Methods

Cells. Vero cells (American Type Culture Collection (ATCC), Manassas, VA, CCL-81) were maintained in medium 199 (Sigma Chemical Company, St. Louis, MO) that was supplemented with 8% fetal bovine serum (Invitrogen, Carlsbad, CA), 1.25 µg/mL fungizone (Invitrogen, Carlsbad, CA) and penicillin-streptomycin, 1000 U/mL and 1 mg/mL respectively (Sigma Chemical Company, St. Louis, MO). Cells were passed weekly using 0.1% trypsin (Sigma Chemical Company, St. Louis, MO) to detach the cells from the flasks. Cell quantification was done by trypan blue exclusion.

Test Chemicals. Twelve of the most prevalent ginsenosides, including the R and S isoforms for the four ginsenosides that had R and S confirmations, were evaluated for anti-herpes simplex activity. These included Rb1, Rb2, Rb3, Rc, Rd, Re, Rf, Rg1, 20(R)-Rg2, 20(S)-Rg2, 20(R)-Rg3, 20(S)-Rg3, 20(R)-Rh1, 20(S)-Rh1, 20(R)-Rh2 and 20(S)-Rh2. Additionally, the ginsenoside metabolites 20(R)-protopanaxadiol and 20(S)-protopanaxadiol were also tested, because of the similarity in structure to 20(R)-Rg3 and 20(S)-Rg3, differing only by the lack of the disaccharide sophorose. Valacyclovir (Sigma Chemical Company, St. Louis, MO), a known anti-herpes compound, was used as a control for herpes inhibition. All compounds derived from *P. ginseng* were obtained from Biopurify Phytochemicals Ltd. (Sichuan, China) and were prepared in DMSO.

Viruses and Quantification. Herpes simplex virus type 1 (HSV-1, MacIntyre strain, ATCC, VR-539) or herpes simplex virus type 2 (HSV-2, ATCC, VR-734) were used in these studies. Virus titer was determined by plaque assay. Briefly, following 2 hour-adsorption of various virus dilutions onto a Vero cell monolayer in a 24-well plate, the medium was removed and cells were overlaid with 1.5% carboxymethylcellulose (Sigma Chemical Company, St. Louis, Mo.) and incubated 48 hours at 37° C. with 5% $CO_2$. After incubation, cells were fixed with methanol, stained with Giemsa (Sigma Chemical Company, St. Louis, Mo.) and plaques were counted. Each virus dilution was prepared in quadruplicate.

The plaque assay procedure also was used to evaluate the percent plaque reduction; the only procedural change was that a constant virus concentration was used (50 plaque forming units (PFU)/well). Plaque reduction was measured by comparing the control (virus only), with valacyclovir (16 µM) with virus or 20(S)-Rg3 (50 µM) with virus. Sample wells were evaluated in quadruplicate. Following the 2 hour-virus adsorption, the methylcellulose-medium containing the same concentrations of valacyclovir or Rg3 was added to the appropriate wells. After 48 hours, plaques were fixed, stained and counted.

Cytotoxicity and Virus Inhibition. All ginsenosides, isomers, and protopanaxadiols were evaluated for toxic effects on Vero cells prior to anti-viral testing. Cells were seeded at 5000 cells/well in a black 96-well plate with clear bottom in a volume of 100 µL and allowed to attach for 24 hours. The

*P. ginseng* compounds were prepared in DMSO at 100 µM and were taken through serial two-fold dilutions to determine the concentration when the rate of cell death was less than 10% compared to control, untreated cells. Each dilution was tested in three wells and all assays were repeated three times. Following a 48 hour-incubation at 37° C. in 5% $CO_2$, 11 µL of PrestoBlue (Invitrogen, Carlsbad, Calif.) was added to each well and the plate was incubated for an additional 30 minutes. PrestoBlue determines cell viability by changing from blue to red as resazurin is reduced to resorufin by viable cells. Following the PrestoBlue incubation, fluorescence was determined by spectrophotometric reading using Soft Max Pro (Molecular Diagnostics, San Jose, Calif., USA).

For cytotoxicity testing, 4 µL of dilutions of the ginsenosides or protopanaxadiols were added to 396 µL of medium 199 and 100 µL of this mixture was added to each of three wells. For anti-viral testing, 4 µL of the non-toxic reagent and 4 µL of HSV-1 or HSV-2 diluted to an MOI of 0.1 were added to 392 µL of medium 199 and 100 µL of this mixture was added to each of three wells. Virus inhibition was determined by comparing the cell death of reagent-exposed cells with cell death of control cells only receiving virus. The 50% inhibitory concentration ($IC_{50}$) was determined through a series of two-fold dilutions and calculation by linear regression analysis.

Time Studies. For virus inhibition studies described above, reagent 20(S)-Rg3 and virus were added to cells simultaneously. To evaluate the potential mode of action of Rg3, various combinations of valacyclovir, Rg3 and HSV-1 were tested at different time periods. The following combinations were evaluated at both one hour and four hours:

Virus applied to cells first (for one hour or four hours), followed by addition of valacyclovir, Rg3 or both valacyclovir and Rg3 to the cells;
Valacyclovir or Rg3 or both valacyclovir and Rg3 applied to cells first (for one or four hours), followed by virus;
Valacyclovir or Rg3 incubated together with virus first for one or four hours then added to cells.

All procedures described for evaluation of virus inhibition were followed in identical fashion as outlined for the PrestoBlue procedure except valacyclovir was used at a constant concentration of 16 µM and 20(S)-Rg3 at 50 µM.

Mouse Susceptibility Study. BALB/c mice and the HSV-1, MacIntyre strain, ATCC VR-539, were used to determine the effectiveness of the 20(S)-Rg3 ginsenoside in preventing mortality in mice caused by infection of HSV-1. On day 1 of the study, four groups consisting of four mice each were injected intraperitoneally with 800,000 PFU of HSV-1, MacIntyre strain, ATCC VR-539. Three of the groups were treated daily with 1 mg/kg, 3 mg/kg, or 10 mg/kg intraperitoneal injections of the 20(S)-Rg3 ginsenoside and one group in the study received no treatment.

Results

Toxicity. All ginsenosides and the closely related metabolites 20(R) and 20(S)-protopanaxadiol were tested for toxic effects on Vero cells. Both protopanaxadiol isoforms were the most toxic compounds and had to be diluted to 12.5 µM to cause less than 10 percent (%) cell death compared to controls (Table 1). Most of the compounds tested resulted in less than 10% cell death when used at 100 µM. 20(S)-Rg3 was determined to effectively inhibit herpes simplex viruses, and additional testing was done to find the concentration of this compound that was toxic to Vero cells, starting at 1000 µM (Table 2). When used at 1000 µM, 20(S)-Rg3 resulted in nearly complete cell death. At 500 µM, an 80 percent death rate occurred for Rg3; but subsequent two-fold dilutions were non-toxic and resulted in lower cell death compared to untreated controls. At concentrations of 250 µM and less, exposure to 20(S)-Rg3 had a proliferative effect on cells or at least enhanced metabolic activity compared to untreated cells. The non-toxic concentration of all compounds shown in Table 1 was used for virus inhibition tests. The known herpes simplex inhibitor valacyclovir was used at 16 µM; this concentration caused 1.2±0.4 percent cell death.

Virus Inhibition. Of all the ginsenosides, isoforms, or metabolites tested, only 20(S)-Rg3 was able to dramatically inhibit HSV-1 (Table 1). While 20(S)-Rh2 inhibited HSV-1 by 46.2%, it was approximately half as effective as 20(S)-Rg3. Given the effectiveness of Rg3, additional investigations were carried out with this molecule. When coupled with virus, one of the ginsenosides, Rf, and the metabolite 20(S)-protopanaxadiol resulted in greater cell death than virus alone, even when used at a non-toxic level.

Due to the significant antiviral activity of 20(S)-Rg3 against HSV-1, 20(S)-Rg3 was also evaluated for inhibition of HSV-2. As shown in Table 3, at 100 µM, Rg3 nearly completely inhibited both of these herpes alphaviruses. At 50 µM, each virus was suppressed by 80%. The $IC_{50}$ of 20(S)-Rg3 was determined to be approximately 35 µM. As a control, valacyclovir had an $IC_{50}$ concentration of 13.2 µM against HSV-1.

Plaque reduction of HSV-1 by 20(S)-Rg3 was also tested to evaluate bioactivity. Table 4 documents the percent reduction of HSV-1 by valacyclovir (used at 16 µM) and Rg3 (50 µM). All wells were infected with the same concentration of virus (approximately 50 PFU each) but only 1.5±0.3 plaques were visible on cells treated with Rg3.

Time Studies. The time of exposure of cells to virus or to bioactive compound was tested. As shown in FIG. 1, when HSV-1 was applied to cells before either valacyclovir (16 µM) or Rg3 (50 µM) were present, there was less inhibition of virus. When virus was present on cells 4 hours prior to Rg3 addition, the percent inhibition was only 50.7±4.4. When cells were exposed to Rg3 prior to HSV-1 addition, the virus was inhibited more effectively. As the length of time for bioactive reagent pretreatment increased to 4 hours, virus inhibition also increased, reaching a maximum percent inhibition of 90.1±11.1 for Rg3.

Figure 2:
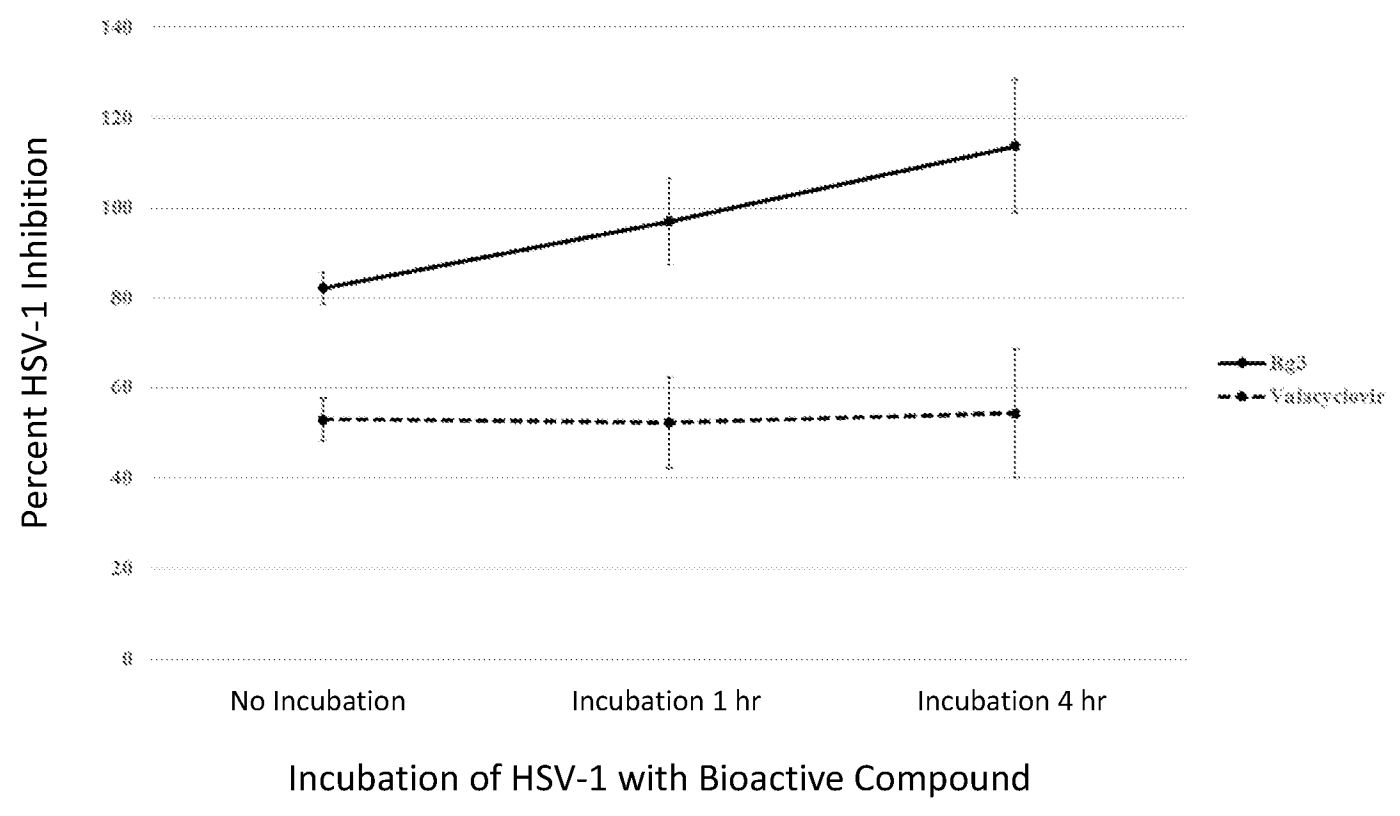

When HSV-1 was incubated together with valacyclovir prior to addition to cells, there was no change in virus inhibition, ranging from 52.3 percent to 54.7 percent from 0 to 4 hours (FIG. 2). As incubation of HSV-1 with Rg3 increased to 4 hours, however, there was a dramatic increase in inhibition of virus to 113.7±14.8 percent. When virus was incubated together with Rg3 and valacyclovir simultaneously for 4 hours, a synergistic effect was evident with percent virus inhibition at 125.3±4.9.

Mouse Susceptibility Study. Four groups with four BALB/c mice in each group were injected with a lethal dose of HSV-1. The control group received no additional treatment and the other three experimental groups received daily doses of 1 mg/kg, 3 mg/kg, or 10 mg/kg 20(S)-Rg3. All of the mice in the control group showed signs of stress: slow to respond to stimuli, sluggishness and squinting of the eyes on day four post injection with HSV-1; beginning to exhibit abdominal distension on day nine post infection; and moribund at day 14 post injection. The experimental groups never showed any signs of stress during the duration of the study.

TABLE 1

Cytotoxicity and Inhibition of HSV-1 by Ginsenosides and Protopanaxadiols.

| Ginsenosides & Protopanaxadiols | Cytotoxicity μM | Percent Inhibition of HSV-1 |
|---|---|---|
| Rb1 | 50 | 23.3 |
| Rb2 | 100 | 26.4 |
| Rb3 | 100 | 30.9 |
| Rc | 100 | 28.6 |
| Rd | 100 | 36.1 |
| Re | 100 | 26.7 |
| Rf | 100 | (38.0) [1] |
| Rg1 | 100 | 13.2 |
| 20(S)-Rg2 | 100 | 44.3 |
| 20(R)-Rg2 | 100 | 25.3 |
| 20(S)-Rg3 | 100 | 90.3 |
| 20(R)-Rg3 | 100 | 22.7 |
| 20(S)-Rh1 | 100 | 14.2 |
| 20(R)-Rh1 | 100 | 26.3 |
| 20(S)-Rh2 | 25 | 46.2 |
| 20(R)-Rh2 | 50 | 12.0 |
| 20(S)-protopanaxadiol | 12.5 | (1.7) |
| 20(R)-protopanaxadiol | 12.5 | 14.4 |

The non-toxic concentration was defined as causing less than 10% cell death compared with controls. To determine cytotoxicity, all compounds were initially tested starting at 100 μM. Subsequent 2-fold dilutions were made as necessary. The non-toxic concentration was used to determine virus inhibition.

TABLE 2

Cytotoxicity of 20(S)-Rg3 on Vero Cells.

| Concentration (μM) | Percent Cell Death |
|---|---|
| 1000 | 99.6 ± 0.02 |
| 500 | 82.3 ± 14.7 |
| 250 | (28.7 ± 1.4) [1] |
| 125 | (22.3 ± 1.8) |
| 100 | (14.3 ± 4.5) |
| 50 | (13.0 ± 3.1) |

[1] Values in parenthesis indicate less cell death than the control.

TABLE 3

Inhibition of Herpes Simplex Viruses by 20(S)-Rg3. The values are the percent inhibition ± the standard error compared to the control cells that were exposed to the viruses but not to Rg3.

| Rg3 Concentration μM | Percent Inhibition of HSV-1 | Percent Inhibition of HSV-2 |
|---|---|---|
| 100 | 90.3 ± 9.9 | 114.7 ± 6.7 |
| 50 | 82.3 ± 3.5 | 81.7 ± 10.3 |
| 25 | 11.0 ± 2.6 | 14.3 ± 3.3 |

TABLE 4

Plaque Reduction of HSV-1. The number of plaques ± the standard error and the percent reduction compared to the control after treatment by valacyclovir or 20(S)-Rg3 are shown.

| | Number of Plaques | Percent Reduction |
|---|---|---|
| Control | 56.7 ± 1.2 | |
| Valacyclovir | 8.1 ± 1.1 | 85.7 |
| 20(S)-Rg3 | 1.5 ± 0.3 | 97.3 |

DISCUSSION

In this study the 12 most prevalent ginsenosides from natural (white) or steamed (red) ginseng were examined as potential inhibitors of HSV-1 and HSV-2. 20(S)-Rg3 demonstrated significant antiviral activity with an $IC_{50}$ of approximately 35 μM against HSV-1 and HSV-2, respectively. Additionally, 20(S)-Rg3 had very low toxicity, with an $IC_{50}$ value of approximately 400 μM against the host Vero cells. With a selectivity of 11-fold, Rg-3 appears to be very promising as an antiviral agent against HSV-1 and HSV-2.

A possible mechanism of 20(S)-Rg3 is suggested in the experiments shown in FIG. 2, where the virus was incubated with the bioactive compounds prior to exposure to host cells. For valacyclovir, there was no difference in anti-viral activity regardless of whether the virus was exposed to valacyclovir prior to infecting cells. This result was expected since valacyclovir is only activated by viral thymidine kinase once the virus is replicating inside the host cell. However, when 20(S)-Rg3 was allowed to interact for 4 hours with the virus prior to exposure to host cells, successful production of virus was reduced over 110%. While all aspects of herpes simplex attachment and penetration of host cells have not been fully elucidated, a good picture of the process has been described. Host receptor heparan sulfate is bound by herpes glycoproteins gB and gC (O'Donnell et al. Virol Sin 2008; 23:383-93), although the need for gC has been questioned (Bender et al. J Virol 2005; 79:11588-97). The next step involves binding of gD and the glycoprotein dimer gH-gL with the Herpes Virus Entry Mediator receptors and nectin-1 or nectin-2, which are cell adhesion molecules (Sedy et al. Nat Rev Immunol 2008; 8:861-73). Given the array of at least five possible attachment glycoproteins, it is reasonable to hypothesize that incubation of HSV-1 with 20(S)-Rg3 prior to exposure to host cells may result in ginsenoside binding with a viral attachment protein, decreasing the opportunity for viral penetration.

The experiments shown in FIG. 1 indicate that the therapeutic effects of 20(S)-Rg3, as well as acyclovir, were strongest when cells were exposed to the bioactive compounds before virus had an opportunity to attach and penetrate its host. These results are consistent with the known mechanism of valacyclovir as a nucleoside analog. Valacyclovir enters cells but remains inactive until HSV is also present. Increased anti-viral activity is seen with pre-exposure of cells to valacyclovir; upon viral infection, valacyclovir is already present, "waiting" to be activated. In terms of 20(S)-Rg3 effects, the data from FIG. 1 also allow another possible contributing mechanism for 20(S)-Rg3 activity. Exposure of endothelial cells to 20(R)-Rg3/20(S)-Rg3 has been reported to result in decreased expression of adhesion molecules, both vascular cell adhesion molecule-1 and intracellular cell adhesion molecule-1 (Hien et al. Pharmazie 2010; 65:699-701). Optimal receptors for HSV attachment include the cell adhesion molecules nectin-1 and nectin-2. Further, Uchida and colleagues (Uchida et al. J Virol 2010; 84:12200-9) investigated HSV-1 attachment and penetration using mutations in gB and gD. When a mutation in gD prevented normal binding with the Herpes Virus Entry Mediator, the virus was still able to penetrate the host cell through an epidermal growth factor receptor. A possible mechanism of 20(S)-Rg3 inhibition of herpes simplex viruses may relate to binding with such alternate receptors since 20(R)-Rg3/20(S)-Rg3 has been reported to down-regulate epidermal growth factor receptor (Joo et al. Chem Biol Interact 2015; 233:25-34).

The mouse susceptibility study in which BALB/c mice were injected with a lethal dose of HSV-1 demonstrated the therapeutic potential of 20(S)-Rg3. 100% mortality was observed in the control group that received no treatment and 0% mortality was observed in the three treatment groups that received therapeutic relevant daily doses of 1 mg/kg, 3 mg/kg, or 10 mg/kg 20(S)-Rg3. That the lowest dose of 20(S)-Rg3 was just as effective as the highest dose of 20(S)-Rg3 reinforces the potential of 20(S)-Rg3 as a therapeutic. Interestingly, a 1 mg/kg dose corresponds to a concentration of 17.8 uM in a typical 70 kg human adult with a blood volume of 5 L.

A synergistic effect occurred when the ginsenoside was used together with valacyclovir, inhibiting virus activity by 125%. These results suggest that using two pharmacological agents with differing modes of action could be effective at inhibiting herpes simplex virus and in combating increasing resistance to acyclovir.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating a herpes simplex virus-1 (HSV-1) infection in a mammal in need thereof, the method comprising administering to the mammal a composition comprising an effective amount of the ginsenoside 20(S)-Rg3, wherein 20(S)-Rg3 is at least 80 wt % of the total weight of ginsenosides present in the composition.

2. The method of claim 1, wherein 20(S)-Rg3 is at least 90 wt % of the total weight of ginsenosides present in the composition.

3. The method of claim 1, wherein the composition further comprises a pharmaceutically acceptable carrier.

4. The method of claim 1, wherein the composition further comprises an anti-herpes viral agent.

5. The method of claim 4, wherein the anti-herpes viral agent is selected from the group consisting of acyclovir, penciclovir, valacyclovir, famciclovir, ganciclovir, valganciclovir, foscarnet, cidofovir, fomivirsen, and combinations thereof.

6. The method of claim 1, wherein the composition is administered orally.

7. The method of claim 1, wherein the composition is administered via inhalation.

8. The method of claim 1, wherein the composition is administered parenterally.

9. The method of claim 1, wherein the mammal is a human.

10. The method of claim 1, further comprising administering to the mammal an anti-herpes viral agent selected from the group consisting of acyclovir, penciclovir, valacyclovir, famciclovir, ganciclovir, valganciclovir, foscarnet, cidofovir, fomivirsen, and combinations thereof.

11. A method of treating a herpes simplex virus-2 (HSV-2) infection in a mammal in need thereof, the method comprising administering to the mammal a composition comprising an effective amount of the ginsenoside 20(S)-Rg3, wherein 20(S)-Rg3 is at least 80 wt % of the total weight of ginsenosides present in the composition.

12. The method of claim 11, wherein 20(S)-Rg3 is at least 90 wt % of the total weight of ginsenosides present in the composition.

13. The method of claim 11, wherein the composition further comprises a pharmaceutically acceptable carrier.

14. The method of claim 11, wherein the composition further comprises an anti-herpes viral agent.

15. The method of claim 14, wherein the anti-herpes viral agent is selected from the group consisting of acyclovir, penciclovir, valacyclovir, famciclovir, ganciclovir, valganciclovir, foscarnet, cidofovir, fomivirsen, and combinations thereof.

16. The method of claim 11, wherein the composition is administered orally.

17. The method of claim 11, wherein the composition is administered via inhalation.

18. The method of claim 11, wherein the composition is administered parenterally.

19. The method of claim 11, wherein the mammal is a human.

20. The method of claim 11, further comprising administering to the mammal an anti-herpes viral agent selected from the group consisting of acyclovir, penciclovir, valacyclovir, famciclovir, ganciclovir, valganciclovir, foscarnet, cidofovir, fomivirsen, and combinations thereof.

* * * * *